United States Patent [19]

Orelup

[11] Patent Number: 4,764,474
[45] Date of Patent: Aug. 16, 1988

[54] METHOD FOR DETECTING A TAGGING COMPOUND

[75] Inventor: Richard B. Orelup, Upper Saddle River, N.J.

[73] Assignee: Morton Thiokol, Inc., Chicago, Ill.

[21] Appl. No.: 77,350

[22] Filed: Jul. 24, 1987

Related U.S. Application Data

[60] Division of Ser. No. 920,902, Oct. 16, 1986, which is a continuation of Ser. No. 562,331, Dec. 16, 1983, abandoned.

[51] Int. Cl.$^4$ ............................................. G01N 33/22
[52] U.S. Cl. ................................... 436/111; 436/27; 436/56; 436/140; 436/139
[58] Field of Search ............... 436/111, 27, 56, 140

[56] References Cited

U.S. PATENT DOCUMENTS

| | | | |
|---|---|---|---|
| 1,898,953 | 2/1933 | Grossman | 260/50 |
| 3,164,449 | 3/1961 | Buxbaum | 44/59 |
| 3,192,117 | 6/1965 | Kaiser et al. | 167/88 |
| 3,435,054 | 3/1969 | Kranz et al. | 260/378 |
| 3,454,604 | 7/1969 | Shown et al. | 260/380 |
| 3,764,273 | 10/1973 | Turner et al. | 23/230 R |
| 3,793,349 | 2/1974 | Johnson et al. | 260/377 |
| 3,883,568 | 5/1975 | Turner et al. | 260/383 |

FOREIGN PATENT DOCUMENTS

| | | | |
|---|---|---|---|
| 1016941 | 9/1977 | Canada | 260/236.25 |
| 1306040 | 9/1962 | France | . |
| 452421 | 8/1936 | United Kingdom | . |
| 1549873 | 8/1979 | United Kingdom | 260/383 |

OTHER PUBLICATIONS

Chemical Abstracts, vol. 107, No. 16, May 7, 1987, p. 708, Abstract No. 144992a, Ito et al., "Magenta Dye for Sublimation-type Thermal Transfer Recording Material".
Chemical Abstracts, vol. 94, No. 14, Mar. 22, 1979, p. 82, Abstract No. 104895c, "1,4-Dihydroxy-2-Alkylaminoanthraquinones".
Chemical Abstracts, vol. 85, No. 20, Jul. 8, 1976, p. 91, Abstract No. 144703j, Hederich Volker, "Anthraquinone Compounds".
Chemical Abstracts, vol. 66, No. 12, Aug. 17, 1963, Abstract No. 47251k, Kazuhiro et al., "Mordant Dyeing of with Antraquinone Dyes".

*Primary Examiner*—Barry S. Richman
*Assistant Examiner*—Amalia L. Santiago
*Attorney, Agent, or Firm*—George Wheeler; Gerald K. White

[57] ABSTRACT

Tagging compounds (which function as both dyes and markers) having the following structures:

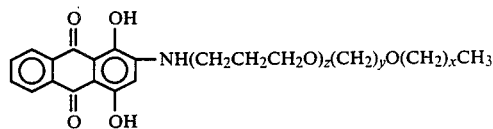

OR

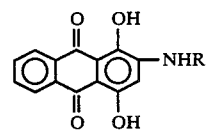

wherein x is an integer between 0 and 3 inclusive, y is an integer between 1 and 3 inclusive, z is 0 or 1, and R is a straight or branched chain hydrocarbon having from 1 to 5 carbon atoms are disclosed. These compounds can be dissolved in a diluent at a concentration of from about 10 percent to about 30 percent, forming a concentrate which can be further dispersed in an organic liquid to form a final concentration of from about 1 ppm to about 15 ppm of said tagging compound in said liquid. Methods for detecting the presence of a tagged compound in an organic liquid are also disclosed.

2 Claims, No Drawings

METHOD FOR DETECTING A TAGGING COMPOUND

This is a divisional of a copending application, U.S. Ser. No. 920,902, filed Oct. 16, 1986, now pending, which in turn is a continuation of copending U.S. Ser. No. 562,331, filed Dec. 16, 1983, now abandoned. The benefit of both prior applications is claimed under Title 35 U.S.C. 120.

The invention relates to compounds and processes for marking or dyeing organic liquids, particularly petroleum based fuels.

BACKGROUND ART

A dye is defined herein as a material lending visible color when dissolved in the dyed product. Examples of dyes which have been used for dyeing organic liquids are Color Index Solvent Red #24, Solvent Red #19, Solvent Yellow #14, Solvent Blue #36, and Solvent Green #3.

A marker is defined herein as a substance which can be dissolved in a liquid to be identified then subsequently detected by performing a simple chemical or physical test on the marked liquid. Markers that have been proposed, or are in use, include furfural, quinizarin, diphenylamine and radioactive materials. (Radioactive materials have not been accepted in Western countries because of special equipment and precautionary measures associated with their handling.)

Dyes and markers (referred to collectively as "tags" herein) are needed to clearly distinguish chemically or physically similar liquids. As one example, fuels are dyed to provide visually distinctive brand and grade denominations for commercial and safety reasons. As another example, some lightly taxed products are tagged to distinguish them from similar materials subject to higher taxes. Furthermore, certain fuels are dyed or marked to deter fraudulent adulteration of premium grade products with lower grade products, such as by blending kerosene, stove oil, or diesel fuel into regular grade gasoline or blending regular grade gasoline into premium grade gasoline. Identification of particular batches of bulk liquids for protection against theft is another valuable function of markers and dyes, particularly for identifying fuels owned by large government, military or commercial consumers. Finally, marketers of brand name products tag their products with dyes or markers to detect substitution of others' products in their distribution system.

Dyes alone are not always adequate to securely and reliably tag liquids. Many dyes are easily removed by unauthorized persons. Furthermore, dyes can be obscured by other natural or added substances (particularly dyes present at low concentrations in a mixture of fuels). Because dyes alone have these shortcomings, a combination of a dye and a marker often is used to tag an organic liquid.

Many commonly used markers are also less than ideal for tagging bulk liquids. Quinizarin and diphenylamine both are fairly sensitive marking materials, with simple detection procedures, but have the disadvantage of poor solubility in nonpolar materials. Their solubility in commonly used petroleum solvents is less than 1%, meaning that an undesirably large volume of a concentrated marker solution must be transported and handled to mark a given volume of fuel. (To encourage rapid and complete dissolution of the marker, it is usually added to the liquid to be marked in the form of a concentrated solution, rather than as a pure compound.)

Furfural has previously been used as a marker for middle distillate fuels. It is extracted by a 10% solution of aniline in acetic acid to form a strongly colored bluish red complex in the lower reagent layer. While quite sensitive, this test has serious disadvantages. First, the slightest contamination of the fuel by residual furfural (which is sometimes used in refining) gives a false positive test. Second, furfural is unstable in certain oils and may not be detectable in such oils after the usual storage period of three to six months. Third, middle distillate fuels tend to discolor appreciably during storage. Some of this discoloration is extracted by aniline acetate and can partially or totally obscure a positive furfural test, particularly if the furfural marked fuel is used to adulterate more expensive or highly taxed unmarked fuel.

As a specific example, furfural has been used in several European countries as a marker for fuel oil at concentrations of 5–10 parts per million (ppm). While certain relatively clean oils give a positive test for as little as 0.5 ppm of furfural, lower quality oils have been observed to give no distinguishable test at concentrations of up to 2 ppm. For such oils the furfural marker cannot be detected in mixtures containing 20%–40% marked fuel. Thus, the less expensive marked fuel can be used in substantial quantities as a diluent without being detected.

Furfural marked fuels have commonly been dyed red, particularly using Solvent Red #19, Solvent Red #24, or related derivatives. But the discoloration previously referred to also obscures the dye, thus preventing visual confirmation that the fuel is tagged.

Recent changes in refining practices further threaten the utility of furfural/red dye combination tagging. In the fairly clean and stable straight run fuels prevalent until recently, furfural is an acceptable marker. But a combination of higher oil prices and sharply increasing demand for diesel fuel as a proportion of the total motive fuel market has necessitated the increasing use of severely cracked heavier grades of crude oil. Severely cracked oils tend to be somewhat unstable, are relatively highly colored when fresh, and tend to destroy the furfural used to mark them. Discoloration and the tendency to destroy the furfural marker both increase as these oils are aged. Tests have shown that 30% to 40% of the furfural is decomposed when it is stored four days in such fuels.

While current practice in many European refineries is production of straight run and cracked fuel oil blends containing 5%–15% cracked product, which will coexist marginally with its furfural marker, it is estimated that the proportion of heavily cracked fuel will exceed 30% in a few years. Under these conditions furfural will be of little or no value as a marker.

The patent literature discloses compounds which are structurally related to the materials disclosed herein as tagging compounds for fuels or other organic liquids. Many of the compounds disclosed herein are novel. The compounds disclosed here which are not novel per se have not been disclosed in the prior art to be useful as a combined dye and marker.

U.S. Pat Nos. 3,764,273 and 3,883,568, the former issued to Turner, et al. on Oct. 9, 1973 and the latter issued to the same inventors on May 13, 1975, disclose 2(2-ethylhexyl)-1,4-dihydroxyanthraquinone:

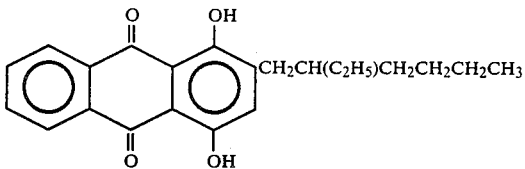

and other substituted anthraquinones in which the depending alkyl moiety has from 1 to 20 carbon atoms, and describes them as being useful as markers for water immiscible organic liquids. But these markers are disclosed to be colorless when employed as markers, and thus do not function both as dyes and as markers at a single concentration.

U.S. Pat. No. 3,192,117, issued to Kaiser, et al. on June 29, 1965; U.S. Pat. No. 3,454,604, issued to Shown et al. on July 8, 1969; U.S. Pat. No. 3,793,349, issued to Johnson, et al. on Feb. 19, 1974; and British Specification No. 1,549,873, published Aug. 8, 1979; respectively disclose the following compounds:

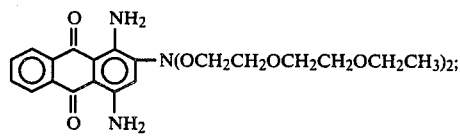

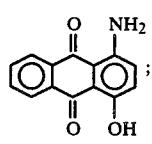

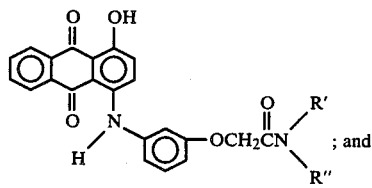

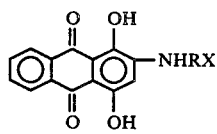

(In the latter compound, R is selected from propyl, isopropyl, or ethyl and X is selected from chloride, bromide, cyanide, or 1 to 4 carbon alkoxy. Specific examples of the amino substituent disclosed in the British specification include the following:

—NHCH$_2$CH$_2$OCH$_3$;

—NHCH$_2$CH$_2$CH$_2$OCH$_3$;

—NHCH$_2$CH(CH$_3$)OCH$_3$; and

—NHCH$_2$CH$_2$OCH$_2$CH$_3$.

The compounds disclosed in the four previously listed patents are respectively disclosed to have utility as hair dyes; dyestuffs; blue dyes for polyester fibers; and pigments for transfer printing on polyesters, polyacrylonitriles or paper. None of these compounds are disclosed to be useful as markers or dyes for organic liquids.

U.S. Pat. No. 3,435,054, issued to Kranz, et al. on Mar. 25, 1969; U.S. Pat. No. 3,164,449, issued to Buxbaum on Jan. 5, 1965; and British Specification No. 452,421, published Sept. 17, 1936; disclose structurally related dyes. The dyes disclosed in the U.S. patents are for fuels, and those in the British specification are for cellulose esters and ethers.

Matsuoka, et al., "A Novel 2-Amination of Quinizarin Promoted by Copper Ions," *Dyes and Pigments* 1:27–37 (1980), teaches synthesis of various 2-amino-1,4 dihydroxyanthraquinones.

SUMMARY OF THE INVENTION

The objects fulfilled by this invention are to provide novel tagging compounds for petroleum fuels and other liquids which:

1. are entirely foreign to the liquids;
2. can be supplied as highly concentrated solutions in compatible solvents;
3. are easily detected by a simple field test;
4. are not obscured by unstable natural components of the liquids;
5. are stable over the anticipated storage life of the tagged liquid (usually three to six months);
6. have identities which can be confirmed by laboratory methods; and
7. act as both a marker and a dye by simultaneously imparting an acceptably intense red color and functioning as a marker at low concentration in the tagged liquid.

These objects are realized by substituted 1,4-hydroxyanthraquinones having the general formula:

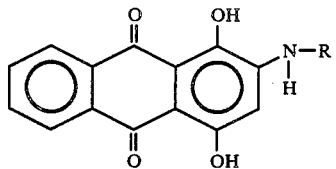

wherein R is an alkyl moiety selected from the group consisting of
(1) moieties having the following structure:

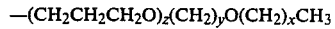

—(CH$_2$CH$_2$CH$_2$O)$_z$(CH$_2$)$_y$O(CH$_2$)$_x$CH$_3$ wherein x is an integer between 0 and 3 inclusive, y is an integer between 1 and 3 inclusive, and z is 0 or 1; and (2) linear or branched hydrocarbons having from 1 to about 5 carbon atoms.

DETAILED DESCRIPTION OF THE INVENTION

One preferred category of tagging compounds according to the invention is that of substituted 1,4-hydroxyanthraquinones having the structure shown previously, wherein the R substituent is an ether moiety and z is one. Specific examples of such compounds which are believed to be novel are:

(1) 2-(methoxyethoxypropylamino)-1,4-dihydroxyanthraquinone; and
(2) 2-(ethoxyethoxypropylamino)-1,4-dihydroxyanthraquinone.

Another preferred category of such compounds is that wherein the R substituent is an ether moiety and z is zero. Specific examples of such compounds which are believed to be novel are:

(3) 2-(butoxypropylamino)-1, 4-dihydroxyanthraquinone; and (4) 2-(propoxypropylamino)-1,4-dihydroxyanthraquinone.

Examples of such compounds whose structure is disclosed in the previously-discussed British Specification No. 1,549,873, but whose utilities as tagging compounds combining the properties of a fuel dye and marker are not believed to be known, are:

(5) 2-(methoxypropylamino)-1,4-dihydroxyanthraquinone;

(6) 2-(methoxyethylamino)-1,4-dihydroxyanthraquinone; and (7) 2-(ethoxyethylamino)-1,4-dihydroxyanthraquinone.

Further examples of such compounds, also believed to be novel, are as follows:

(8) 2-(methoxypropoxypropylamino)-1,4-dihydroxyanthraquinone;

(9) 2-(ethoxymethylamino)-1,4-dihydroxyanthraquinone;

(10) 2-(ethoxymethoxypropylamino)-1,4-dihydroxyanthraquinone;

(11) 2-(ethoxypropylamino)-1,4-dihydroxyanthraquinone;

(12) 2-(propoxyethylamino)-1,4-dihydroxyanthraquinone;

(13) 2-(butoxyethylamino)-1,4-dihydroxyanthraquinone;

Specific examples of compounds in which the R substituent is a straight or branched chain hydrocarbon are as follows:

(14) 2-(methylamino)-1,4-dihydroxyanthraquinone;
(15) 2-(ethylamino)-1,4-dihydroxyanthraquinone;
(16) 2-(n-propylamino)-1,4-dihydroxyanthraquinone;
(17) 2-(n-butylamino)-1,4-dihydroxyanthraquinone;
(18) 2-(n-pentylamino)-1,4-dihydroxyanthraquinone;
(19) 2-(2-propylamino)-1,4-dihydroxyanthraquinone;
(20) 2-(2-butylamino)-1,4-dihydroxyanthraquinone; and
(21) 2-(t-butylamino)-1,4-dihydroxyanthraquinone.

One of ordinary skill in the art, using the preceding generic disclosure and specific examples as a guide, can determine other species within the scope of the present invention. Mixtures of species are also contemplated to be within the scope of the present invention.

These dual function tags generally are crystalline solids in pure form, but may be conveniently supplied as concentrates containing 10%–30% of the pure compound dissolved in one or more high boiling aromatic solvents or in mixtures of high boiling aromatic solvents with co-solvents such as alkyl phenols. The solvent selected also is not critical, provided that it is sufficiently soluble in the tagged fuel to permit a desirably large final proportion of the tagging compound to be incorporated in the fuel, and provided tha solvent does not interfere with storage or use of the tagged fuel and detection of the tagging compound. Specific examples of high-boiling aromatic solvents useful herein are SURESOL #190, primarily comprising a mixture of methyl naphthalenes, available from Koch Refining Co., Corpus Christi, Tex.; and commercial grade xylene (mixed isomers). Specific examples of alkyl phenols useful herein are commercial xylenols (which typically contain some phenols and cresols); ortho -sec-butyl phenol; and para-nonyl phenol. The fuel to be tagged can also be used as a solvent.

The compounds are typically added to liquids to be tagged at a concentration of 10–15 parts per million of the pure compound, or from about 40 ppm to about 100 ppm of the concentrate. Such concentrations provide a color intensity comparable to that commonly required of dyed fuels. However, fuels containing the minimum detectable and visible concentration of the pure tagging compound (less than 1 ppm) or a larger concentration of the tagging compound are also within the scope of the invention. The amount of tagging compound is not critical, provided that it is dissolved or stably suspended in the solvent and is as concentrated as its solubility permits.)

Fuel tagged as disclosed herein can be detected in fuel mixtures containing as little as 5%–10% tagged fuel, whether visually, in field inspection tests, or in the laboratory. Detection is possible even in the presence of 25%–50% highly cracked fuel oils or gasolines, and the novel marker dyes taught herein are found to be essentially unchanged after at least three months' storage in the same fuels.

FIELD PROCEDURE FOR DETECTING TAGGING COMPOUND

A convenient sample (20–50 ml) of fuel suspected to contain tagged fuel is shaken or otherwise contacted with approximately 1/10 its volume (2 to 5 ml) of an alkaline, fuel immiscible reagent in an appropriately narrow glass vial or bottle of 30–120 ml capacity, then allowed to stand. The reagent comprises from about 20% to about 60% glycerine, from about 20% to about 40% water, and from about 10% to about 50% of an organic amine. Two preferred reagents for use herein are disclosed in the Examples below. The alkaline, fuel immiscible reagent is specific to these markers, meaning extraction of otherwise interfering alkaline reactive colored fuel components is minimized. The reagent settles to the bottom and is colored bluish red if marked fuel is present. If the sample contains no marker, the reagent layer remains colorless (or very slightly yellow for some fuels). The distinction is very apparent even at low marker levels.

LABORATORY PROCEDURE FOR DETECTING TAGGING COMPOUND

A semiquantitative laboratory procedure for the determination of tagged fuel content comprises passage of a measured sample (conveniently 25 ml) of suspected tagged fuel through an activated alumina column, to which all natural and added colorants adhere. Following this, selective column washes remove essentially all colored materials except the marker, which is finally removed, collected and brought to volume. Absorbance of the colored solution is measured instrumentally and related to marker concentration.

EXAMPLES

The following examples are provided to describe how to make and use the invention and to demonstrate its utility. The scope of the invention is not limited by these examples, but is defined by the claims following this specification.

EXAMPLE 1

2-(methoxypropylamino)-1,4-dihydroxyanthraquinone was prepared as follows: 60 grams of 1,4-dihydroxyanthraquinone, 15.5 grams of boric acid, and 89 grams of methoxypropylamine were slurried in 125 ml of water. The slurry was stirred and heated to 65° Celsius, and a strong stream of air was bubbled through it. These conditions were maintained about nine hours, or until thin layer chromatography of the reaction mixture failed to isolate any, 1,4-dihydroxyanthraquinone.

The (now uniform) liquid mass was poured into a solution of 150 ml. concentrated hydrochloric acid and 300 ml. water, while stirring. Crystals were given time to agglomerate, then the crystals were filtered, washed until free of acid, and dried. The melting point of the resulting product was 140 degrees Celsius.

A similar procedure is followed to form 2-(methoxyethoxypropylamino)-1,4-dihydroxyanthraquinone (melting point: 114 degrees Celsius) and the other 2-amino substituted -1,4 dihydroxyanthraquinones disclosed herein from the corresponding amine and 1,4 dihydroxyanthraquinone.

EXAMPLE 2

30 grams of 2-(methoxyethoxypropylamino)-1,4-dihydroxyanthraquinone were dissolved in a mixture containing 35 grams ortho-sec-butyl phenol and 35 grams of commercial xylene. The resulting clear dark red solution remained pourable, stable and uniform at temperatures down to −18° C. for an indefinite period.

Forty grams of this solution were dissolved in 1000 liters of straight run #2 heating oil to form a red solution defined as 100% marked fuel. The color intensity, measured instrumentally at its wavelength of maximum absorption (512 nm), was equal to the color intensity of a solution containing five grams of Solvent Red #19 (Color Index 26050) per 1000 liters of heating oil, measured at the wavelength of maximum absorption (520 nm) for Solvent Red #19.

EXAMPLE 3

Fifty milliliters of the 100% marked heating oil of Example 1 were shaken in a 120 ml oil sample bottle with 5 ml of a reagent comprising (by weight):
54% Glycerine
26% Water
20% Methoxyethoxypropylamine
After standing a few seconds, the reagent layer sank to the bottom and was observed to be colored intensely red.

A 50 milliliter sample of the same straight run heating oil containing no marker or dye was subjected to the same test. The reagent layer remained colorless or very slightly yellowish.

EXAMPLE 4

The 100% marked heating oil of Example 1 and an unmarked control were stored together at ambient temperature in the dark for a period of three months. The colorimetric test of Example 1 and the marker field test of Example 2 were repeated, with essentially the same results.

EXAMPLE 5

A mixture containing 10% by volume marked heating oil according to Example 1 and 90% unmarked straight run #2 motor diesel fuel was tested according to the procedure of Example 2. A red color again was observed in the reagent layer and was distinctly different from the color of the reagent used to test the unmarked fuel.

EXAMPLE 6

Examples 1–4 were repeated except the fuel consisted of a commercial blend comprising 75% straight run fuel and 25% of a severely cracked fuel.

The visual and spectrophotometric color tests were sometimes modified by employing untagged fuel oil in the reference cell to account for the contribution of the natural oil colors, but the comparative marker field tests were usable without modification. Substantially the same results were observed.

EXAMPLE 7

7.5 grams of 2-(methoxypropylamino)-1,4-dihydroxyanthraquinone and 9.0 grams of 2-(methoxyethoxypropylamino)-1,4-dihydroxyanthraquinone were dissolved to form a clear red solution in a solvent mixture comprising 41.7 grams p-nonyl phenol and 41.7 grams of mixed xylenes. The solution remained pourable, stable and uniform at temperatures down to −18° C. for an indefinite period.

67 grams of this solution were easily dissolved in 1000 liters of straight run #2 heating oil to form a red solution defined as 100% marked heating oil. Its color intensity was equal to that of a solution of 5 grams Solvent Red #19 in 1000 liters of the same oil, each color intensity being measured at the wavelength of maximum absorption.

EXAMPLES 8–11

Examples 2–5 were repeated using the dye solution of Example 6, with essentially the same results.

EXAMPLE 12

7.6 grams of 2-(methoxypropylamino)-1,4-dihydroxyanthraquinone and 9.0 grams of 2-(methoxyethoxypropylamino)-1,4-dihydroxyanthraquinone were dissolved in a solvent mixture comprising 41.7 grams of commercially available xylenols and 41.7 grams of commercial xylene to form a clear red solution. 67 grams of this solution were easily dissolved in 1000 liters of regular grade leaded gasoline, with essentially the same result as in Example 6.

EXAMPLES 13 and 14

Examples 2 and 3 were repeated, using the tagged gasoline of Example 11 as the 100 per cent unmarked fuel. The results were essentially the same.

EXAMPLE 15

A mixture containing 10% by volume marked regular gasoline (made according to Example 11) and 90% premium grade leaded gasoline was tested according to the procedure of Example 2. The test for the tagging compound was clearly positive, and the resulting reagent layer was readily distinguishable from the colorless or very slightly yellowish reagent layer which resulted when the same test was performed on completely unmarked premium grade leaded gasoline.

EXAMPLE 16

25 ml of a commercial blended #2 heating oil comprising 75% straight run fuel and 25% of a severely cracked fraction, and containing 67 parts per million of the red tagging composition defined in Example 6, was gravity percolated through a column of activated alumina which had a 10 millimeter diameter and was 50 millimeters long. The activated alumina was ALCOA Type F-20, chromatographic grade. The column was then washed with a small portion of isooctane to remove adhering heating oil. At this point the column was colored strongly yellow-brown, particularly near the top, while the percolated fuel was clear. (The column color intensity and distribution depends on the natural color content of the fuel sample.) Successive washes of acetone and ethyl alcohol were passed through the column, and eluted the yellow and brown natural colors of the fuel.

The tagging compound remained in the column as a purple zone, concentrated at the column head or somewhat diffused along much of its length, depending on the fuel's composition.

An eluant mixture having the following composition (by weight):

25% Glycerine
35% Water
40% Cyclohexylamine was gravity percolated through the column. All of the tagging compound could normally be separated using less than 10 ml of the eluant, and the total eluant was diluted to 10 ml in a volumetric flask.

The eluant was subsequently clarified by passing it through an 0.45-0.60 micron particle retention membrane and its absorbance was measured at 556-557 nm. By reference to a calibration curve derived by measuring the absorbance of fuels having known marker concentrations, marked fuel content was determined.

Other primary amines such as n-amylamine, n-butylamine or methoxyethoxypropylamine were substituted in the above reagent without changing the result substantially, although maximum color stability was obtained with cyclohexylamine.

What is claimed is:

1. A method for detecting a tagging compound having a structure selected from the group consisting of:

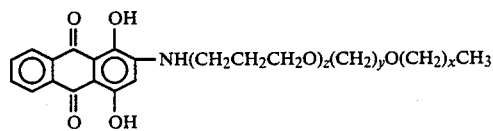

wherein x is an integer between 0 and 3 inclusive, y is an integer between 1 and 3 inclusive, and z is 0 or 1, and

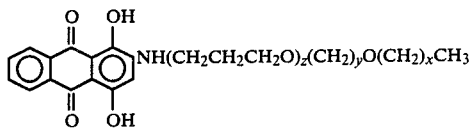

wherein R is selected from linear or branched hydrocarbons having from 1 to about 5 carbon atoms, comprising the steps of:
   A. providing a sample suspected to contain said tagging compound;
   B. contacting said sample with a reagent comprising:
      i. from about 20 weight percent to about 60 weight percent glycerine;
      ii. from about 20 weight percent to about 40 weight percent water; and
      iii. from about 10 weight percent to about 50 weight percent of an organic primary amine to form an admixture therewith;
   C. allowing the admixture to form a sample phase and a reagent phase; and
   D. determining whether said reagent phase develops a substantially bluish red or red color, thereby indicating the presence of said tagging compounds.

2. A method for detecting a tagging oompound having a structure selected from a group consisting of:

O OH
‖
⟨anthraquinone⟩—NH(CH₂CH₂CH₂O)_z(CH₂)_yO(CH₂)_xCH₃
‖
O OH wherein x is an integer between 0 and 3 inclusive, y is an integer between 1 and 3 inclusive, and z is 0 or 1 and O OH
‖
⟨anthraquinone⟩—NHR
‖
O OH wherein R is selected from linear or branched hydrocarbons having from 1 to about 5 carbon atoms, and mixtures thereof, comprising the steps of:
   A. providing a sample of an organic liquid suspected to contain said tagging compound;
   B. passing said sample through an activated alumina chromatographic column;
   C. washing said organic liquid from said column with a solvent therefor;
   D. washing the natural colors of said organic liquid from said column with a solvent therefor; and
   E. determining whether a substantially purple zone is formed in said column, thereby indicating the presence of said tagging compounds.

* * * * *